US00PP12235P2

(12) United States Plant Patent
Drewlow

(10) Patent No.: US PP12,235 P2
(45) Date of Patent: Nov. 27, 2001

(54) NEW GUINEA IMPATIENS PLANT NAMED 'OVATION ORANGE SWIRLS'

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,515

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grunberg
(74) *Attorney, Agent, or Firm*—Webb Ziesenheim Logsdon Orkin & Hanson, P.C.

(57) ABSTRACT

A distinct cultivar of Impatiens plant named Ovation Orange Swirls, characterized by its orange petals with radiating lighter color streaks creating a swirl effect, deep green leaves, early flowering, long-lasting flowering, self-branching and vigorous habit.

1 Drawing Sheet

The present invention relates to a new and distinctive cultivar of Impatiens plant, botanically known as *Impatiens Hawkeri,* commercially known as New Guinea Impatiens, and known by the cultivar name of 'Ovation Orange Swirls'. Ovation Orange Swirls was developed in a controlled breeding program by crossing Mikkelsen Seedling No. 95-1109-6 (seed parent) with Mikkelsen Seedling No. 95-1109-1 (pollen parent). Both parents are proprietary breeding lines which have not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguish the new Impatiens from both its parent varieties and other cultivated Impatiens of this type known and used in the floriculture industry:

1. Ovation Orange Swirls has Red-Orange Group 43B colored flowers with Red Group 56B radiating out from the center of the petals and is uniquely colored with Celebrette Peach (U.S. Plant Pat. No. 10,108) being more of a salmon-orange (Red Group 40B) with a small area of Red Group 56B in center.
2. Ovation Orange Swirls has a much larger flower at 7.0 to 7.5 cm in diameter while the flower of Celebrette Peach is 5.5 to 6.0 cm in diameter.
3. Ovation Orange Swirls has deep green leaves while Celebrette Peach has dark green leaves with a red-purple cast.
4. Ovation Orange Swirls has a mounded growth habit while Celebrette Peach has a more upright habit of growth.
5. Ovation Orange Swirls has light green venation in leaves and the midrib is light green except on old leaves which have a touch of red-purple while Celebrette Peach has red-purple venation and midrib.
6. Ovation Orange Swirls has much less red pigmentation in the stems than Celebrette Peach.
7. Ovation Orange Swirls has a white stigma and style while Celebrette Peach has a red-purple stigma and style.
8. Ovation Orange Swirls has oval shaped leaves and Celebrette Peach has a lanceolate leaf shape.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. The plants were grown at 16° C. night temperatures, under 3000 to 4000 foot candles of light and 200 ppm nitrogen, 75 ppm potassium, and 200 ppm phosphorous with nutritional trace elements added. Habit of growth, foliage coloration, leaf variegation, size of leaves, and flower size will be greatly influenced by nutritional and environmental conditions.

Color references are made to The Royal Horticultural Society Colour Chart except where general terms of ordinary dictionary significance are used.

Parentage: A controlled cross between female parent Mikkelsen Seedling No. 95-1109-6 and male parent Mikkelsen Seedling No. 95-1109-1.

Propagation:

(*A*) *Type cutting.*—Stem tip 15 mm long will develop to 4 to 5 cm long in 18 to 21 days.

(*B*) *Time to root.*—8–10 days at 23° C. summer; 10–12 days at 20° C. winter.

(*C*) *Rooting habit.*—Heavy, fibrous.

Plant description:

(*A*) *Form and habit of growth.*—Mounded, self-branching, intermediate in height, flowers open over the top of leaf canopy; continuous flowering; vigorous growing herb. Average height is 18 to 22 cm and average width is 40 to 45 cm. Internode length 5 to 6 cm but is highly variable. Pedicel is Yellow-Green Group 147D, stem is Yellow-Green Group 147C, and internode is Yellow-Green Group 147C. Pedicel length is 3.5 cm.

(*B*) *Foliage description.*—Deep green with young leaves having light green midrib and older leaves developing red-purple midrib and no leaf variegation. (1) Size: 8 to 9 cm long and 3.5 to 4 cm wide on average mature leaf. (2) Shape: Oval with acuminate apex and acute base. (3) Texture: Both upper and lower surfaces are glabrous. (4) Margin: Finely serrated with fine cilia. (5) Color: Young foliage, top side is Yellow-Green Group 147A, underside is Yellow-Green Group 146A; Mature foliage, top side is Yellow-Green Group 147A, underside is Yellow-Green Group 148B. (6) Venation: Pinnate, upper side is Yellow-Green Group 146C and lower side is Yellow-Green Group 146B. (7) Young midrib is Yellow-Green Group 147D and mature midrib is also Yellow-Green Group 147D.

(*C*) *Branching.*—The branching is naturally occurring. Lateral branching at base: 5 or more lateral branches. Lateral branch length is 14 to 17 cm but is highly variable.

Flowering description:

(*A*) *Flowering habits.*—Flowers continuously from leaf whorl in a progressively orderly manner with one flower per leaf axil. When the last flower in a leaf whorl opens the first flower in the leaf whorl above starts to open. It takes 5 to 7 days for a mature bud to fully open and the flower may last two weeks or longer depending on the environment. The time to first flower is approximately 8 weeks from root cuttings. The flower is self-cleaning.

(*B*) *Natural flowering season.*—Indeterminant and continuous; quantity of flowering increases with increasing levels of light.

(*C*) *Flower bud.*—Ellipsoidal; flowers perfect; spur is 4.5 cm long on mature bud, with the throat behind the ovary and originating from the major sepal. Bud length is 18 to 20 mm, and bud diameter is 16 mm. Spur is Red-Purple Group 59D, spur tip is Yellow-Green Group 146D, flower bud is Red Group 44C just before opening, and eye is Red Group 56B.

(*D*) *Flowers borne.*—On individual green with red-purple cast pedicels 3.5 cm long from a whorl of usually four leaves. Flowering progressively around the whorls as buds and leaves develop. Leaf axils have one flower each.

(*E*) *Quantity of flowers.*—Numerous because of self-branching nature of plant and the long-lasting flower characteristic.

(*F*) *Diameter of flower.*—7.0 to 7.5 cm. Flower Depth: 5 mm.

(*G*) *Petals.*—(1) Shape: Heart. (2) Color: Top side when opening is Red Group 43B with Red Group 56B at center of petal and radiating out into the petal, fading to Red Group 43B with large areas of Red Group 56B; underside is Red-Orange Group 34B. (3) Number of petals: Five. (4) Size of petals: Standard: 5.5 cm wide and 3.0 cm long, two equal lobes with moderate cut. Wings: 3.5 cm wide and 3.5 cm long, two unequal lobes with moderate cut. Keel: 4.5 cm wide and 4.0 cm long, two unequal lobes with deep cut.

(*H*) *Reproductive organs.*—(1) Stamens: Five in number. (a) Anther: Hooded shape, color is Yellow-White Group 158A with a Red Group 46C cast. (b) Pollen color: Yellow-White Group 158C. (2) Pistils: (a) Stigma: Five, segmented column, color is White Group 155B. (b) Style color: White. (c) Ovaries: Five in number, size is 7 mm when immature, color is Yellow-Green Group 147A.

(*I*) *Fertility.*—The plants are fertile, but do not normally set seed under greenhouse or garden conditions, unless in a controlled crossing program.

Disease resistance: No significant disease or insect problems to date.

OTHER IMPORTANT CHARACTERISTICS

1. Self-branching, early flowering nature allows cultivar to be grown in 10 cm pots but is also vigorous enough to be grown in 15 to 25 cm containers as well.

2. Minimal fading of older flowers, large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Orange Swirls, as illustrated and described.

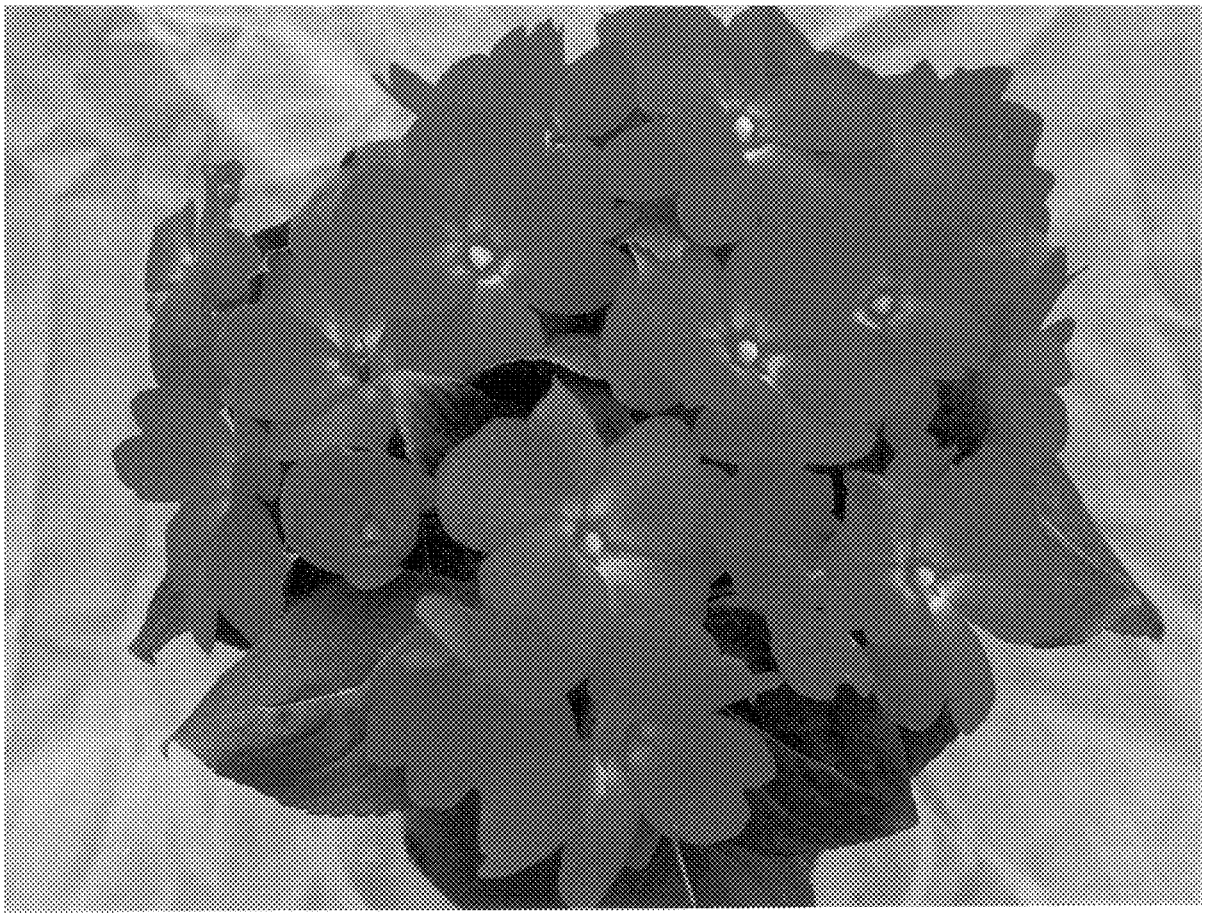

* * * * *